US005766200A

United States Patent [19]

Mazurek et al.

[11] Patent Number: 5,766,200
[45] Date of Patent: Jun. 16, 1998

[54] ROTATABLE ENDOSCOPIC SHAVER WITH POLYMERIC BLADES

[75] Inventors: William F. Mazurek, Palm Harbor; Warren Barrett, Palmetto, both of Fla.

[73] Assignee: Linvatec Corporation, Largo, Fla.

[21] Appl. No.: 547,051

[22] Filed: Oct. 23, 1995

Related U.S. Application Data

[63] Continuation of Ser. No. 323,599, Sep. 30, 1994, abandoned, which is a continuation of Ser. No. 58,504, May 6, 1993, abandoned.

[51] Int. Cl.$^6$ ............................................. A61B 17/00
[52] U.S. Cl. ............................................. 606/170; 604/22
[58] Field of Search ............................. 606/167, 159, 606/170, 171, 180; 604/22

[56] References Cited

U.S. PATENT DOCUMENTS

| | | |
|---|---|---|
| 4,603,694 | 8/1986 | Wheeler. |
| 4,606,335 | 8/1986 | Wedeen. |
| 4,646,738 | 3/1987 | Tratt. |
| 4,735,605 | 4/1988 | Swartz. |
| 4,815,462 | 3/1989 | Clark. |
| 4,883,458 | 11/1989 | Shiber. |
| 4,886,061 | 12/1989 | Fischell et al.. |
| 4,886,490 | 12/1989 | Shiber. |
| 4,979,939 | 12/1990 | Shiber. |
| 5,041,082 | 8/1991 | Shiber. |
| 5,135,481 | 8/1992 | Nemeh. |
| 5,135,531 | 8/1992 | Shiber. |
| 5,152,744 | 10/1992 | Krause et al. ............ 606/180 |
| 5,154,724 | 10/1992 | Andrews. |
| 5,282,821 | 2/1994 | Donahue ............ 604/22 |
| 5,593,416 | 1/1997 | Donahue. |

FOREIGN PATENT DOCUMENTS

| | | |
|---|---|---|
| 0445918 | 9/1991 | European Pat. Off.. |
| 0 481 760 | 4/1992 | European Pat. Off.. |
| 38 28 478 | 5/1989 | Germany. |
| 1718792 | 3/1992 | U.S.S.R.. |
| 9304634 | 3/1993 | WIPO ............ 606/180 |

*Primary Examiner*—Michael Buiz
*Assistant Examiner*—William Lewis
*Attorney, Agent, or Firm*—Gene Warzecha

[57] ABSTRACT

A rotatable shaver having inner and/or outer non-metallic elongated blades for use in endoscopic surgical procedures. In one embodiment a rotatable, elongated non-metallic inner tubular member is disclosed for use with a non-rotatable elongated metallic outer tubular member, the inner member having a flexible, non-metallic tubular body, a proximal hub and a distal tip provided with a cutting edge. The elongated tubular body of the inner member may be extruded or molded from a polymeric or composite material and may be bonded to or integrally formed with either the hub, the distal cutting tip or both. In one embodiment, the entirety of the rotatable inner tubular member (i.e. hub, tubular body and cutting tip) may be integrally formed as a single unit. In another embodiment, the outer tubular member is formed with a non-metallic tubular sheath within which a metallic or non-metallic inner member may rotate.

10 Claims, 3 Drawing Sheets

ROTATABLE ENDOSCOPIC SHAVER WITH POLYMERIC BLADES

This is a continuation application of application Ser. No. 08/323,599, filed Sep. 30, 1994, now abandoned which is a continuation application of application Ser. No. 08/058,504 filed May 6, 1993 now abandoned.

BACKGROUND OF THE INVENTION

1. Field of the Invention

The present invention pertains to surgical cutting instruments and, more particularly, to surgical cutting instruments having an elongated inner tubular cutting member rotating about its axis within an elongated outer tubular member having a cutting window at its distal end which cooperates with the inner member to cut, resect or abrade bodily tissue, the resulting loose tissue being aspirated through the lumen of the inner member.

2. Description of the Prior Art

The use of elongated surgical cutting instruments has become well accepted in performing closed surgery such as arthroscopic or, more generally, endoscopic surgery. In closed surgery, access to the surgical site is gained via one or more portals, and instruments used in the surgical procedure must be elongated to permit the distal ends of the instruments to reach the surgical site. Some conventional surgical cutting instruments (shavers) for use in closed surgery are rotary powered and have a straight, elongated outer tubular member and a straight, elongated inner tubular member concentrically disposed in the outer tubular member. The inner and outer members both separately and jointly are sometimes referred to in the art as "blades". The outer member has a distal end having an opening in the end or side wall (or both) to form a cutting port or window and the inner member has a distal end disposed adjacent the opening in the distal end of the outer member. The inner member is easily insertable into and removable from the outer member to facilitate cleaning or interchanging parts. Each of the elongated members has a hub or termination at its proximal end in order to attach the components to a rotary drive means. The distal end of the inner tubular member has a cutting means or cutting edge for engaging tissue via the opening in the distal end of the outer tubular member. In many cases (but not all) this distal cutting means cooperates with the opening in the outer member to shear, cut or trim tissue. In some cases, such as abrading burrs, the opening in the outer member merely allows access to the tissue and does not otherwise cooperate with the cutting means. The term "cutting edge" or "cutting means" as used herein is intended to include abrading (e.g. burrs) and other devices whether or not there is any traditional cutting or shaving action, and whether or not there is any cooperative shearing action. The inner tubular member is rotatably driven about its axis from its proximal end, normally via a handpiece having a small electric motor which is controlled by either finger actuated switches on the handpiece, a foot switch or switches on a console supplying power to the handpiece. The distal end of the inner tubular member can have various configurations depending upon the surgical procedure to be performed, and the opening in the distal end of the outer tubular member would then have a configuration adapted to cooperate with the particular configuration of the distal end on the inner tubular member. For example, the inner and outer tubular members can be configured to produce whisker cutting, synovial resection, arthroplasty burring or abrading, side cutting, meniscus cutting, trimming, full radius resection, end cutting and the like, and the various configurations are referred to generically as cutting means. The loose tissue resulting from the cutting, resecting or abrading procedure is aspirated through the hollow lumen of the inner tubular member to be collected via a vacuum tube communicating with the handpiece.

The aforementioned elongated surgical cutting instruments have also been produced in angled configurations in which the axes of the distal tips of the inner and outer members are aligned and offset or bent at a fixed angle relative to the axes of the proximal ends of the aligned inner and outer members. Examples of such fixed-angle, rotary surgical instruments are shown in U.S. Pat. No. 4,646,738 (Trott), assigned to the assignee hereof, and in European Patent Application 0 445 918 (Krause et al.). In other respects the operation of these fixed-angle shavers is largely the same as that of the straight shavers described above. Known fixed-angle shavers are generally produced with only one offset angle—usually 15°. Recently a variable-angle rotary shaver system has been introduced (described in a co-pending patent application assigned to the assignee hereof) in which the outer tube may be bent by a user to a user-selected angle while still enabling the inner tube to be selectively inserted into and removed from the outer tube. The angled shavers have a bend with a radius of curvature on the order of two inches. Tighter radii would be desirable.

In straight, fixed-angle and variable-angle prior art rotary shavers the inner tubular member has a proximal inner hub shaped to mate within an outer hub situated at the proximal end of the outer tubular member when the two members are assembled. The outer hub serves to lock the outer tubular member to the handpiece while the inner hub is adapted to mate with the motor drive shaft. Since most conventional rotary shavers utilize reusable handpieces with disposable shaver blades, the materials used to make the disposable blades must be cost-effective without adversely affecting performance. Consequently, the inner and outer hubs are generally molded plastic components while the bodies of the inner and outer tubular members are generally made of a biocompatible metal (generally 300 series stainless steel). The latter material is used in prior art inner tubular members because of the necessity to form sharp cutting means at the distal end of the inner member and because of the necessity to transmit a satisfactory amount of torque from the motor to the distal cutting means. The outer tubular member is made from metal in order to adequately hold the rotating inner member and resist any bending or kinking which would prevent rotation of the inner member.

In straight shaver configurations the elongated metallic tubular body of the inner member is generally integrally formed with the cutting means and the proximal end of the body is adhesively, thermally or ultrasonically bonded or otherwise affixed to the plastic hub. In the case of fixed-angle rotary shavers, however, a coupling device is interposed between the body and the cutting means. These prior art angled devices employ an outer member identical to that used in straight configurations (although angled to receive the bendable inner member) while the inner member is made from a metallic tubular body joined to the inner hub, a metallic distal cutting tip and some coupling means to join the two. In the aforementioned European patent application, for example, the coupling means is metallic and integrally formed with the body and tip, the coupling means being merely a portion of the inner member which is provided with relief apertures formed in the cylindrical surface to enable the inner member to bend as it rotates. In this embodiment, the metallic tubular body of the inner member is thermally bonded or otherwise affixed to the plastic hub as in the previously mentioned straight configuration.

Another fixed-angle shaver is known in which the tubular body of the inner member comprises a hollow metallic shaft affixed to the plastic hub, a metallic distal cutting tip and a coupling means formed of a plurality of counter-wound coiled metallic springs bonded to and interposed between the body and the tip. Such an embodiment is disclosed in the aforementioned U.S. Pat. No. 4,646,738 (Trott).

Another fixed-angle shaver is known in which the inner member has a plastic hub bonded to a metallic tubular body, a metallic distal tip and a coupling means formed of a single coil spring covered with a flexible plastic sleeve bonded to and interposed between the body and the tip.

The only known variable-angle shaver system has recently been introduced by Linvatec Corporation, 11311 Concept Boulevard, Largo, Fla. 34643 under the trademark MERLIN. This device incorporates a flexible inner member similar to that disclosed in the aforementioned U.S. Pat. No. 4,646,738 (Trott) and incorporates a unique, user-bendable outer tube.

One disadvantage of known coupling members is their inability to transmit sufficient torque at high rpm's through angles much greater than 25°. As the benefits of angled shavers have been more and more widely appreciated, the angular limitation of prior art angled shavers has become a disadvantage to be overcome. It would, therefore, be advantageous to produce an angled rotary shaver capable of operation at angles greater than 25°.

In each known prior art system the requirement for adequate torque transmission along the inner member from the motor to the distal tip and the requirement for maintaining the sharpness of the cutting edge at the distal tip have been achieved by the use of metallic inner members formed almost entirely from biocompatible metallic materials such as stainless steel. The cost of obtaining and fabricating these materials into inner members is significant even though the combined inner and outer members are intended to be disposable. While the cost is significant even in the straight variety of shaver, the cost increases substantially in the fixed and variable-angle shavers because of the additional complexity involved in these devices. The coupling members of each of the known prior art angled rotary shavers are relatively complex when properly assembled to address the requirements of adequate torque transmission, sufficient lubricity to enable sustained operation at high rpm and sufficient sharpness. The number of component parts (springs, bearing sleeves, tubular bodies, cutting tips, etc.) and their assembly adds to the cost of these devices. It would be advantageous to produce both straight and angled rotatable shaver systems with fewer and/or less costly disposable components.

Known angled shavers are limited in the amount of bending they can tolerate while still satisfactorily transmitting torque to the cutting tip. The limit is about 20°–25° and it would be desirable to produce angled shavers capable of operating with bends greater than 25°.

Another requirement imposed upon rotatable shavers is the necessity to maintain close tolerances between inner and outer members in order to maximize efficiency of operation. Obviously, such close tolerances must be balanced with the need to minimize friction to reduce heat and wear. This is generally done with the use of either lubricants or bearing surfaces—in either case adding to the cost of the device. In the case of angled shaver systems, the necessity to include bearing surfaces is even greater. Additionally, some angled shavers enable the inner member to bend within the outer tube by a configuration which often produces some gaps in the surface of the coupling means of the inner member resulting in a decrease of vacuum through the lumen of the inner member thereby compromising the ability of the device to aspirate tissue shavings through the lumen. This has been overcome in some instances by the use of a flexible polymeric sleeve situated over the bendable, coupling means portion of the inner member thus sealing any gaps while also providing a bearing function. The use of a solid cylindrical polymeric sleeve over a spring in some fixed-angle shavers may obviate the need for an encircling polymeric bearing sleeve. However, such bendable portions have less torque transmitting ability than other versions. The concern about maintaining close tolerances, adequate lubricity and vacuum sealing adds to the cost and complexity of prior art shavers and it would be advantageous to produce an inner member in which the disadvantages associated with these parameters could be minimized.

The rotatable inner members used in known angled shavers are either costlier than comparable straight, unbendable inner members or are not as efficient in transmitting torque. (Some prior art bendable inner members have torque transmission capability which is significantly—up to 50%—less than the straight counterpart.) This is most likely attributable to the coupling member. Nevertheless, this difference makes it necessary for manufacturers of these systems to produce both straight and bendable versions of inner tubular members—creating an undesirable inventory burden. It would, therefore, be advantageous to produce an elongated, rotatable tubular inner member which is less costly than conventional non-bendable inner members and which can be used either in a straight outer tubular member or in an angled outer tubular member without significant loss in its torque transmission ability.

It is also an object of this invention to produce an elongated rotatable inner tubular member having at least a non-metallic tubular body of a biocompatible polymeric or composite material that is more easily bonded to the hub of the inner member and is less costly to obtain and manufacture than conventional metallic materials.

It is also an object of this invention to produce an elongated rotatable inner tubular member in which a portion or the entirety of the inner member (i.e. hub, tubular body and cutting tip) may be fabricated in a single manufacturing process.

It is yet another object of this invention to produce a rotatable inner tubular member in which two or more of the primary components of the inner member (i.e. hub, tubular body and cutting tip) may be integrally formed together.

It is another object of this invention to produce a rotatable inner tubular member in which the material from which the tubular body of the inner member is fabricated enables the assembly of the inner member within an outer member without the necessity for additional lubricating or bearing means.

It is another object of this invention to produce a flexible, rotatable inner tubular member having a tubular body and coupling means integrally formed together from a biocompatible polymeric or composite material capable of being sufficiently lubricated without additional lubricating or bearing surfaces and which may then be bonded to a hub and a distal tip, thus producing a flexible inner member having no more than three parts.

It is also an object of this invention to produce a disposable inner tubular member for a rotary shaver, the inner member capable of being used in a straight or angled configuration.

It is yet another object of this invention to produce a flexible, rotatable inner tubular member capable of use at angles greater than those (i.e. approximately 25°) possible with conventional angled shavers.

It is an additional object of this invention to produce an elongated rotatable inner tubular member for an angled rotary shaver system in which the coupling member interposed between the tubular body at the proximal end of the inner member and the distal tip of the inner member is a non-perforated integral extension of the tubular body.

It is an object of this invention to produce an elongated outer tubular member having a tubular body of a biocompatible polymeric or composite material able to be used in a straight or angled configuration with an elongated rotatable inner member.

It is also an object of this invention to produce elongated inner and outer members of rotatable shavers utilizing polymeric or composite materials which are able to be sterilized by at least one conventional sterilization method used for medical devices.

SUMMARY OF THE INVENTION

These and other objects of the invention are achieved by the preferred embodiment described herein which is a rotatable elongated inner shaver blade for use with a non-rotatable outer elongated tubular shaver blade, the inner blade comprising a non-metallic elongated tubular body having a proximal end and a distal end. An engagement means (hub) is attached to the proximal end of the tubular body for attaching it to a means for rotating it relative to the outer blade. A cutting means is provided at the distal end of the tubular body. In one embodiment the non-metallic tubular body and the engagement means (hub) are integrally formed or otherwise fabricated together as a single unit and the cutting means is attached to the distal end of the unit. Alternatively, the non-metallic tubular body and the cutting means could be integrally formed together and the engagement means (hub) attached to the proximal end. Another embodiment comprises the body, hub and tip all being integrally formed together as a single unit.

Materials suitable for use in these various embodiments include any suitable biocompatible polymeric or composite material having particular characteristics of flexibility and torsional strength. The polymeric materials could be, for example, Lexan® (a polycarbonate resin composition), Ultem® (a polyetherimide resin composition), PEEK (polyetherether ketone) or any other thermoplastic or thermoset material having such characteristics. The composite materials could be a combination of a suitable resin base with any one of a variety of fillers, reinforcing fibers and the like, provided the combination results in an end product having acceptable flexibility and torsional strength. An example of a suitable composite would consist of a polyurethane resin base with Kevlar® reinforcing fibers.

The invention also includes an outer tubular member formed of suitable polymeric or composite materials. The various parts of the outer member (body, hub and window) could be formed similarly to the inner member as described above.

The invention also includes the method of manufacturing a rotatable shaver comprising the steps of providing a polymeric or composite material having a shear strength in the range of approximately 10,000–75,000 pounds/square inch, forming this material into an elongated tubular body having a proximal end and a distal end and providing an engagement means at the proximal end. In the case of an inner member, the engagement means is a means to attach the member to a source of rotation and the method further comprises the step of providing a cutting means at the distal end of the inner member. In the case of an outer member the engagement means is a means to attach the member to a non-rotating handpiece and the method further comprises the step of providing a window at the distal end of the outer member.

DESCRIPTION OF THE PREFERRED EMBODIMENT

Figure 1:
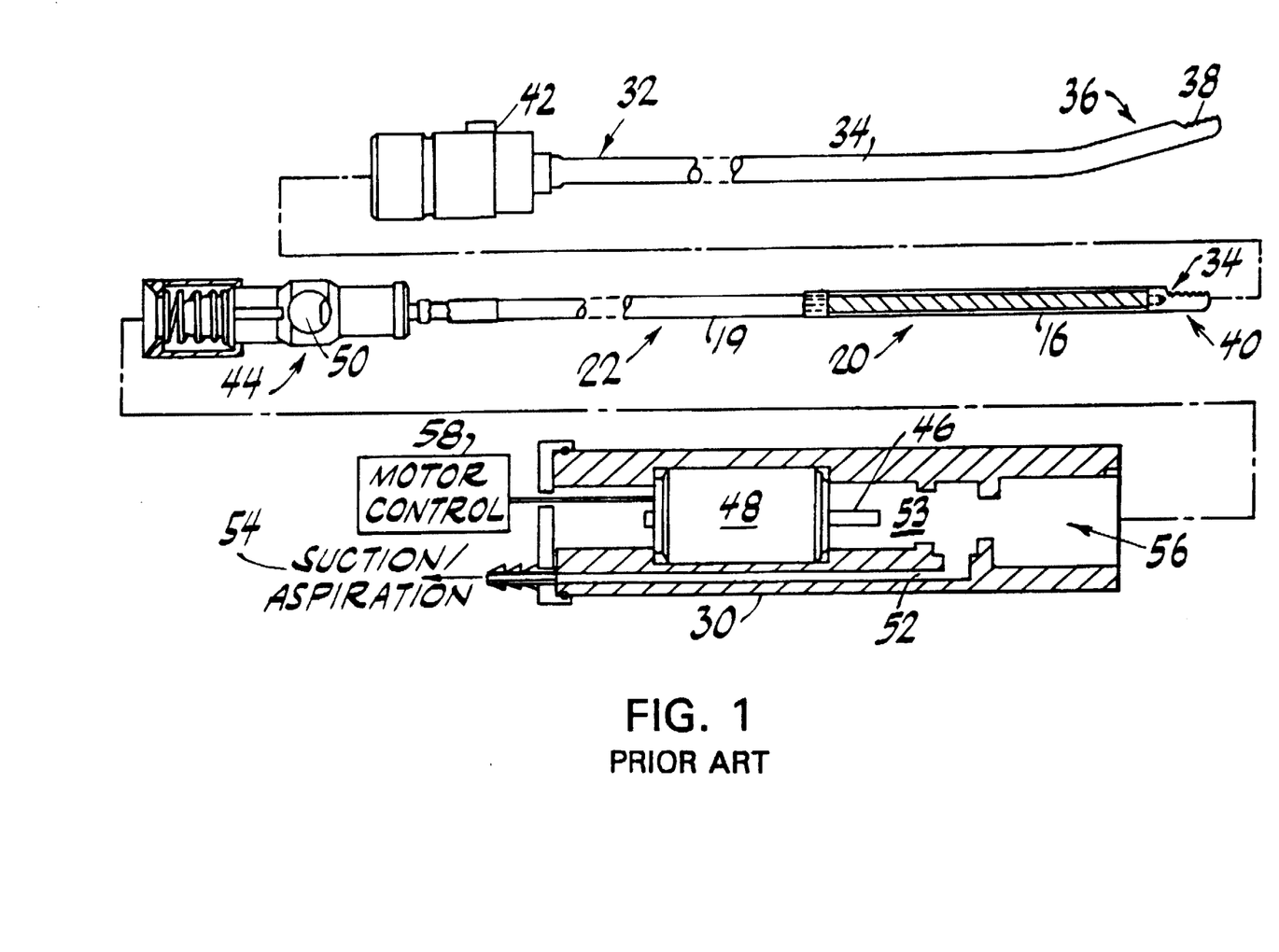
FIG. 1 shows an exploded broken partially sectional view of a prior art instrument comprising a handpiece, a torque-transmitting rotatable inner member with a hub, and an outer non-rotatable sheath with a corresponding hub.

As shown in FIG. 1, one example of a prior art angled rotary surgical instrument includes a handle or handpiece 30, a flexible torque-transmitting rotatable inner tubular member 22 and a rigid outer tubular member or sheath 32. While the tubular bodies of the prior art inner and outer tubular members 22 and 32 are metallic, it will be understood below that the present invention discloses non-metallic inner and/or outer tubular members. Inner member 22 has a plastic hub or engagement means 44, a rigid tubular body 19, a flexible coupling section 20 and a distal cutting means 34. The coupling section 20 includes three concentric, coiled springs, as described in the aforementioned Trott patent, encased within a tubular polymeric sleeve 16 as described in a co-pending application assigned to the assignee hereof. Outer member 32 has a plastic hub or engagement means 42, a rigid tubular body 34 and a distal window opening 38. As indicated by the dot-dash lines in FIG. 1, the flexible torque-transmitting inner member 22 slides within the outer member 32 such that the rotating cutting means 34 at the distal tip 40 of the inner member is situated adjacent cutting window 38 at the distal tip 36 of the rigid outer member 32.

The instrument is assembled for use by inserting the distal tip of inner member 22 into the proximal end of hub 42 of outer member 32 and sliding hub 42 into recess 56 of handpiece 30 so that hub 44 engages an inner corresponding recess 53 in handpiece 30 and so that motor shaft 46 of motor 48 engages hub 44. At that point the rotatable inner member 22 fits within the interior of stationary outer member 32 with the cutting means 34 exposed at the distal end of the outer member 32. When motor 48 is subsequently actuated by motor control 58, the torque-transmitting inner member rotates, rotating cutting means 34 relative to stationary cutter window 38, thereby forming an effective cutting instrument. Suction or aspiration may then be provided at 54 to withdraw or flush debris from the surgical site. The aspiration is provided via the lumen extending the length of the inner member 22 by way of a port 50 in hub 44 communicating with a passage 52 in the handpiece 30.

In the prior art device, fluid-impermeable sleeve member 16 covers the flexible coupling section 20 to provide a bearing function and allow suction or aspiration applied to the proximal end of the inner member 22 to be effectively communicated to the distal end thereof despite any gaps or slots or openings that may be present in the coupling section. Since the flexible coupling of the inner member comprises a number of substantially circumferential slits formed between the spiral-wrapped wire members, if the distal cutting window becomes clogged or obstructed, the condition known as "blow-by" or unrecoverable loss of suction may occur in the absence of sleeve 16. All known prior art coupling members require attention to this characteristic because of the perforated nature of the coupling.

Figure 2:
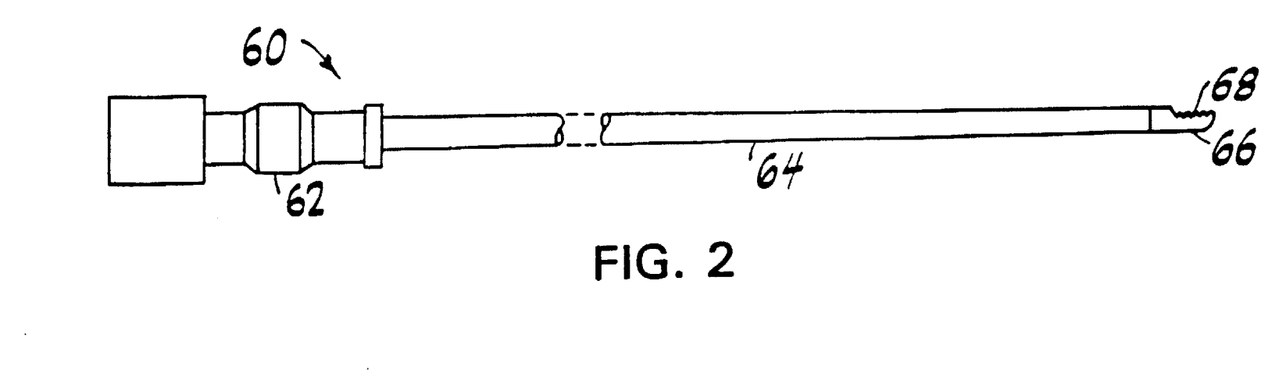
FIG. 2 is a side elevation view of a rotatable inner member constructed in accordance with the principles of this invention in a straight configuration.
Figure 3:
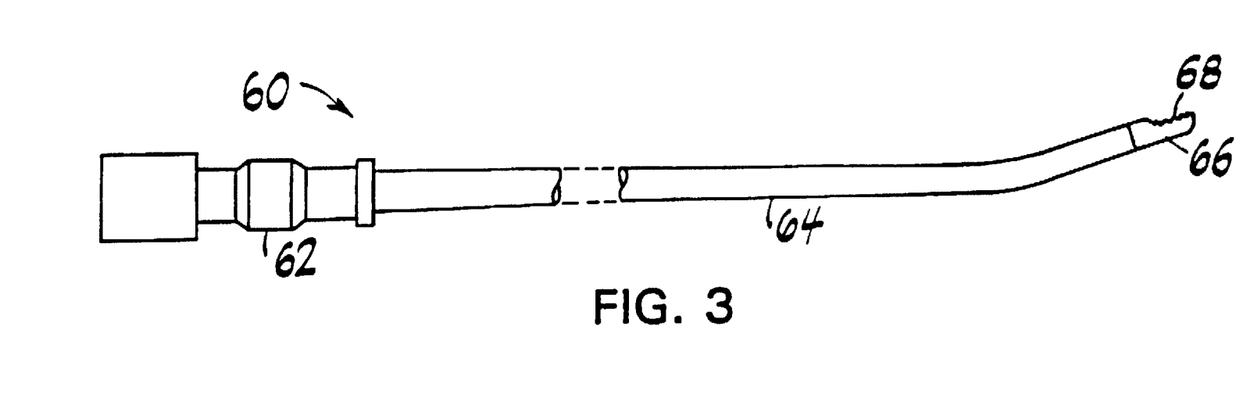
FIG. 3 is a side elevation view of the rotatable inner member of FIG. 2 shown in a curved configuration.
Figure 4:
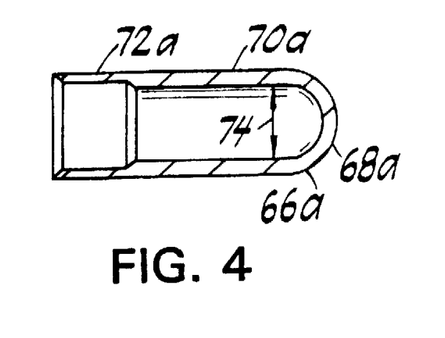
FIGS. 4, 5 and 6 are cross-sectional views of alternate embodiments of a cutting shell which may be attached to the distal end of a non-metallic rotatable inner member.
Figure 5:
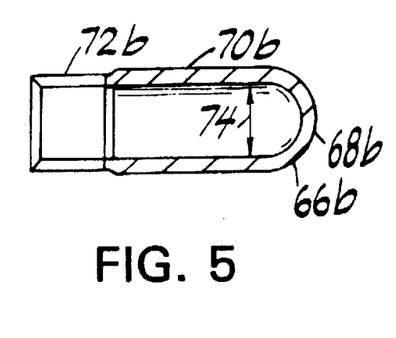
Figure 6:
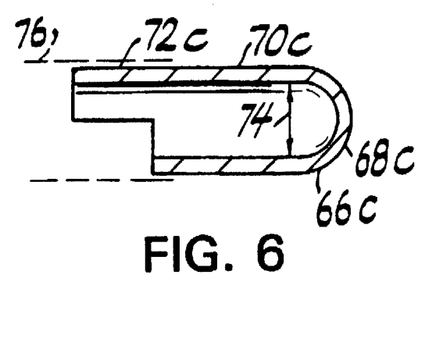

The foregoing description relates to known prior art devices. The invention is an improvement of these known devices and the preferred embodiment of the invention is shown in FIG. 2 comprising a much simplified inner tubular member 60 having a plastic hub 62 at its proximal end, a non-metallic elongated tubular body 64 and a distal metallic cutting means 66 provided with a cutting edge 68. Hub 62 may be a conventional polycarbonate hub used in prior art inner members. As will be understood below with reference to the alternate embodiment shown in FIG. 7, the invention enables use of a simpler proximal end which eliminates the need for a conventional hub by replacing it with an integral engagement means. Body 64 is a solid-walled, non-perforated tubular body formed of a flexible, non-metallic material that enables member 60 to be rotated about its axis and to transmit torque from the motor via hub 62 to cutting means 66. The rotational speed range may vary from zero to several thousand rpm. Cutting means 66 may be made of a non-metallic material integrally formed with tubular body 64 or may be a separate metallic or non-metallic component. The primary requirements for cutting means 66 are that it be capable of providing a cutting edge 68 (in any one of a variety of shapes such as a plurality of teeth as shown in FIG. 3, a straight edge, etc.) and that it be capable of being securely joined—adhesively or otherwise—to the distal end of tubular body 64 so that sufficient torque may be transmitted through the inner member to accomplish its intended function. In the preferred embodiment the cutting means is a separate piece formed of non-galling stainless steel. The piece itself—sometimes referred to as a shell—is conventional and has a rounded front end at the distal end of a cylindrical tubular body and an open rear end at the proximal end of the cylindrical body. Three different embodiments of cutting means 66 suitable for use with the invention are shown in FIGS. 4, 5 and 6 numbered 66a, b and c, respectively. Each cutting means 66a, b and c has a rounded distal tip 68a, b and c, respectively, a cylindrical wall 70a, b and c and a proximal end 72a, b and c. The rounded tips 68a, b and c may be removed in certain applications in the process of forming conventional rotary shaver cutting edges (not shown). Also, any one of a variety of cutting edges may be formed into the wall 70a, b or c. The inner diameter 74 of cutting means should be approximately as big as the lumen of the inner tubular member to be attached to the cutting means. The proximal ends 72a, b and c of the shell are adapted to engage and be joined to the distal end of the inner tubular body. The junction may be formed by making the proximal end of the shell fit around (e.g. 72a) or into (e.g. 72b) the end of the non-metallic tubular inner member as shown in FIGS. 4 and 5, respectively. In either case, one or more of the facing surfaces on the shell and the inner member forming the junction could be knurled or otherwise treated to enhance the strength of the junction. Also, some mechanical interlocking arrangement could be provided as shown in FIG. 6 wherein part of the peripheral wall at the proximal end 72c of the shell is removed to form a rectilinear shape. This proximal end is then adapted to engage a correspondingly shaped distal end (not shown) formed in the inner tubular member. The facing edges of the uniquely shaped junction could then be bonded together. An optional cylindrical sleeve (metallic, polymeric or composite) such as shown in phantom at 76 could overlap both the shell and the tube to enhance the strength of the junction if necessary. The sleeve could be a separate piece or could be injection molded with a metallic cutting shell or integrally formed with a non-metallic cutting shell. Any adhesive or epoxy used to join any of the cutting means and tubular members must obviously be biocompatible.

The variety of possible cutting means 66 is shown only to demonstrate that numerous configurations are suitable for use in the invention disclosed herein. The particular choice depends on the ultimate choice of sizes, materials and torque strengths desired.

The invention obviates the need for a separate junction or coupling between a straight metallic rigid shaft and a flexible coupling member as is necessary in the prior art devices to transmit torque around a bend. The fact that body 64 is non-perforated avoids the disadvantage of the prior art angled shavers in that there are no gaps or slits at the bend of the inner member which adversely affect the aspiration function of the device.

Note that tubular body 64 is flexible and, therefore, bendable along its entire length. However, the actual portion of body 64 which is bent as shown in FIG. 3 depends on the bend created in the outer member into which inner member 60 is inserted. The flexibility of the inner tubular body enables it to follow whatever bend is created in the outer member (up to the flexibility limit of the material chosen for the inner tubular body)—even bends in more than one direction like an "S" curve—while still being able to transmit torque to its distal end. Indeed, while the preferred embodiment disclosed herein incorporates a non-metallic inner member having a polymeric or composite tubular body in cooperation with a conventional bendable outer member having a body made of stainless steel, the invention encompasses the use of such an inner member with an outer member made of either metallic or non-metallic material. That is, the outer member could also be made of a bendable polymeric or composite material provided it is less flexible than the material used in the inner member. The relative rigidity of the inner and outer members may be varied in many ways which will be understood by those skilled in the art. Changes in wall thickness or materials are among the possible ways to control the relative rigidity of the inner and outer members.

An additional advantage of the invention is that the same inner member structure may be used for straight shaver configurations as for angled configurations because the cost of producing the inner blade in accordance with the invention is less than the cost of producing a conventional straight inner member. While known angled inner members could also be used in straight configurations, the cost of these devices makes such use impractical.

Various materials may be used to form the inner and/or outer tubular members in accordance with the principles of this invention. These materials may be broadly classified as either polymeric or composite materials, the former category including numerous thermoplastic and thermoset materials which are distinguished from the latter category by being homogenous. The composite materials may be considered non-homogenous in that such materials generally have a matrix or resin base into which some filler or reinforcing material is placed to create a hybrid. The material suitable for forming inner tubes according to the invention may be chosen from a group of high strength polymer or composite materials which have sufficient shear strength to adequately carry the torsional load (i.e. not fail under normal use) and, in an angled configuration, a bend moment low enough that it will not create excessive friction when a non-metallic inner tubular member is run inside an angled outer tubular member. The material must also be capable of being either attached to or formable into a hub or an engagement means in order to connect the inner member to a drive motor. The material must also be capable of being attached to or formable into a cutting shell.

The same materials may be suitable for use in forming the outer tubular member. However, when used as an outer tubular member, some requirements may vary such that different non-metallic materials may be suitable. For example, outer tubular members need not carry the same torsional load as the inner member.

Several polymeric materials (described below) have been found suitable for inner tubular body 64, all of which have some similar characteristics such as sufficient flexibility to enable the distal tip to bend up to and beyond 25° from the axis of the straight portion, on a two inch radius, while being able to be rotated about its axis at speeds up to several thousand rpm. While the inner member is flexible enough to enable it to be easily inserted into and removed from an angled outer member (bent at 25°), under some circumstances the angle to which the outer tube is bent may be so great that it may need to be straightened somewhat in order to enable removal of the inner member. The materials have sufficient lubricity to minimize friction and generation of heat within the bend or between the inner and outer members in general. It has been found that within the general category of polymeric materials, those having a shear strength on the order of 10,000–75,000 pounds per square inch are suitable materials for making the tubular body of inner member 60. In the particular configurations shown in the drawings, there is a relationship between the wall thickness of the tubular body of the inner member and its torsional strength. With any given material, the torsional strength is proportional to the wall thickness. Therefore, for particular applications, suitable torsional strength of varying amounts may be achieved by materials having shear strengths within the aforementioned limits merely by changing the dimensions of the tubular body.

Table I, Material Properties, lists various characteristics of stainless steel and other polymeric and composite materials. The stainless steel characteristics are shown merely as a reference point to identify characteristics associated with prior art rotatable shavers. The various polymeric materials listed (Lexan 121, Ultem 1000, Ultrapek (PAEK—polyalphaetherketone) and (PEEK—polyetheretherketone) and the composite material (Vectra® A130) are listed only to show examples of some materials suitable for use in the invention. This is not intended to be an exhaustive list. It should be noted that Vectra® (discussed below) is a liquid crystal polymer material but is identified as a composite since the material is somewhat unique and since the latter term is broadly used herein. Table II, Design Properties, lists various parameters resulting from the particular material characteristics when embodied in tubes of varying dimensions. Table II shows arbitrary tube dimensions (outside diameter×inside diameter) associated with the materials identified in Table I. Given the particular tubular dimensions, conventional calculations were employed to determine the moment of inertia, polar inertia, sectional modulus, bend moment, deflection load and torsional strength. Table II clearly shows that polymeric and composite materials can transmit as much torque as certain metallic tubular configurations. As will be shown below with respect to the various Examples, the ability to transmit torque from the proximal end of a tubular inner member to the cutting shell is quite dependent on the bond between the cutting shell and the tubular member. Different attachment methods may be utilized to increase the torque transmission values shown in the Examples.

The following Examples have been constructed from some of the polymeric materials listed in the Tables to demonstrate the benefits of the invention. The various Examples described below were assembled with a drop of Z-Lube lubricant (available from Zimmer, Inc., Warsaw, Ind.) between the inner and outer tubular members in the area of the bend. Such lubrication may or may not be necessary in order to achieve the objects of this invention. It should be noted that some polymeric or composite materials may have many desirable properties for bending but may need additional lubricity to enhance performance. Such lubricity may be provided by applying a coating having a low coefficient of friction or a bearing sleeve, etc.

EXAMPLE 1

Polycarbonate (Lexan 121) tubing was extruded using standard polymer processing techniques. Approximate dimensions for this tubing were 0.132"OD×0.093"ID. A shoulder approximately 2 mm long was machined on the inside diameter of the distal end of the tubing and it was cut to a length of 14 cm. A non-galling stainless steel cutting shell of a conventional size (0.375 inches long, 0.1305 OD×0.115 ID) was epoxy bonded to the shoulder at the distal end of the inner tube. The proximal end of the shell was cylindrical and was provided with a shoulder sized to mate with the shoulder at the distal end of the tube (See FIG. 4). A standard injection molded polycarbonate inner drive hub was epoxy bonded to the proximal end of the inner tube using conventional techniques described by the manufacturer (Tra-Bond, Inc., 55 North Street, Medford, Mass. epoxy #FDA-22). Five such inner tube assemblies were made and each was placed in a metallic outer tube assembly bent to an angle of 25° (on a 2 inch radius) and run at approximately 1000 rpm for 4 to 5 minutes. The inner tube assemblies were then placed in a 15° outer tube assembly and then torque tested to failure in a conventional torque testing apparatus to determine torsional strength. The average failure load was approximately 2.2 in-lb of torque. Failure occurred at the epoxy bond at the shell.

EXAMPLE 2

The same techniques were followed as in Example 1 with the same materials except that a shoulder was machined on the outside diameter of the distal end of the tubing. Five such units were tested to failure as above. The average failure load was approximately 2.5 in-lb of torque and the failure occurred at the epoxy bond at the shell.

EXAMPLE 3

The same techniques were followed as in Example 2 with the same materials except that the standard injection molded inner drive hub was adhesively bonded to the proximal end of the inner tube using techniques described by the manufacturer (Loctite, Inc., adhesive #403). This inner tube assembly was placed in the standard outer tube assembly. Five such units were tested to failure as above. The average failure load was approximately 1.0 in-lb of torque and the failure occurred at the adhesive bond at the shell.

EXAMPLE 4

Polyetherimide (ULTEM 1000) tubing was extruded using standard polymer processing techniques. Approximate dimensions for this tubing were 0.128"OD×0.093"ID. A shoulder approximately 2 mm long was machined on the outside diameter of the distal end of the tubing and it was cut to a length of approximately 14 cm. A non-galling stainless steel cutting shell was epoxy bonded to the distal end of the inner tube. A standard injection molded polycarbonate inner drive hub was epoxy bonded to the proximal end of the inner tube using techniques described by the manufacturer (Tra-Bond, Inc. epoxy, #FDA-22). Five such inner tube assemblies were made and each was placed in a metallic outer tube assembly bent to an angle of approximately 25° (on a 2 inch radius) and run as above. The units were tested to failure as above. The average failure load was approximately 1.6 in-lb of torque and the failure occurred at the epoxy bond at the shell.

EXAMPLE 5

The same techniques were followed as in Example 4 with the same materials except that the metal cutting shell was adhesively bonded to the distal end of the inner tube and the inner drive hub was adhesively bonded to the proximal end of the inner tube using techniques described by the manufacturer (Loctite, Inc. adhesive #403). Five such units were tested to failure as above. The average failure load was approximately 1.3 in-lb of torque and the failure occurred at the adhesive bond at the shell.

EXAMPLE 6

PEEK (polyetheretherketone) tubing was obtained from Zeus Industrial, Orangeburg, S.C. Approximate dimensions of this tubing were 0.125"OD×0.093"ID. A shoulder was machined on the outside diameter of the distal end of the tubing and it was cut to the correct length. A non-galling stainless steel cutting shell was epoxy bonded to the shoulder at the distal end of the inner tube. A standard injection molded inner drive hub was epoxy bonded to the proximal end of the inner tube using techniques described by the manufacturer (Tra-Bond, Inc. epoxy, model #FDA-22). Five such inner tube assemblies were placed in the standard outer tube assembly and then tested to failure to determine torsional strength. The average failure load was approximately 1.0 in-lb of torque. Failure occurred at the epoxy bond at the shell.

EXAMPLE 7

The Ultem and PEEK tubes of Examples 4 and 6 were recovered and the bonding area of each tube was cleaned off. A metal cutting shell was bonded to shoulder at the distal end of each tube using a different epoxy # EP21 LV from Master Bond, Inc., Hackensack, N.J. The average failure of the Ultem tubes occurred at 1.98 in-lb (out of four samples) and the average failure of the PEEK tubes occurred at 1.76 in-lb (out of four samples). All failures occurred at the bond at the shell.

Several composite materials have also been identified as suitable for inner tubular body 64 as well as the outer tubular body. A Kevlar®/resin combination is one example of a suitable composite material. A variety of ceramic materials may also be suitable. The composite materials may generally have flexibility characteristics at least as good (i.e. high flexibility) as the polymeric materials and additionally are able to be formed with a structure having an anisotropic molecular orientation which enables adequate torque transmission while also enabling large angular bends. The composites generally include a resin or other non-metallic polymeric base combined with a filler such as glass, glass fibers, metal particles or strands, carbon, ceramic, other polymers, etc. The term "non-metallic" as used herein is intended to cover even composite materials having metallic filler or reinforcing materials.

EXAMPLE 8

A composite tube with the approximate dimensions of 0.125" OD×0.100" ID was fabricated using Kevlar® fibers. This composite tube was then attached to holding fixtures and torque tested to failure. Failure of the composite occurred at 3.0 in-lb.

One advantage of the invention is that the use of polymeric or composite materials to form the tubular body of the inner member may be extended to include the hub and the cutting tip, thus enabling the entirety of the inner member to be molded from the same material. Examples of such suitable manufacturing processes could be extrusion, molding, vacuum bagging, preimpregnation with polymer (prepreg), laminating, die cutting, thermo-forming, etc. All such processes are referred to herein as "molding" since they all involve forming an amorphous, flowable material into a discrete shape through the use of a tool or die. One composite material that has shown suitability for use in producing at least a one-piece hub/tubular body (with a cutting tip to be added on) is Vectra®—a liquid crystal polymer available from Hoechst Celanese, Chatham, N.J. This material facilitates injection molding long thin tubes without polymer knit lines which would be formed with most other polymer materials.

Figure 7A:
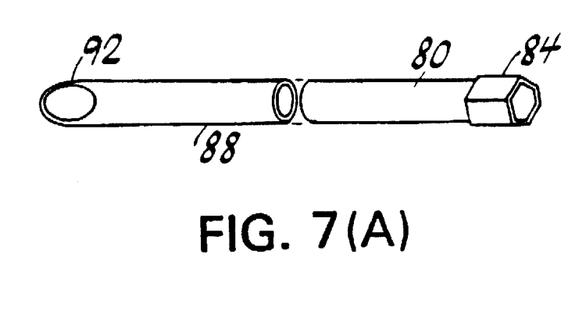
FIGS. 7(a) and 7(b) are diagrammatic views of alternate embodiments of a non-metallic inner and outer blade.
Figure 7B:
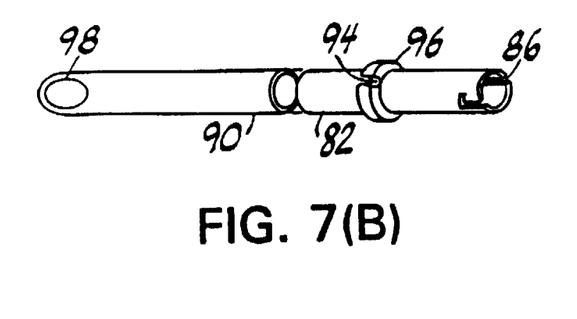

An alternate embodiment of the invention is shown in FIGS. 7(a) and 7(b) disclosing a configuration of entirely moldable inner and outer tubular members 80 and 82, respectively. The hubs used on conventionally shaped inner and outer members are replaced by engagement means 84 and 86, respectively, integrally formed with the tubular bodies 88, 90 of the inner and outer members. The term "engagement means" is intended to broadly include conventional hubs as well as integral means such as 84 and 86. The handpiece with which engagement means 84 and 86 are intended to work is not shown and could be easily produced by one skilled in the art.

Engagement means 84 may be a hexagonal proximal portion integrally formed at the proximal end of body 88. This rectilinear shape could easily be driven by a complementarily shaped socket (not shown) attached to the drive shaft of the motor and the handpiece. The distal tip 92 could be provided with some cutting edges (not shown) in order to produce a workable inner member. The outer tube 82 has an engagement means 86 at its proximal end which may be, for example, a bayonet type locking mechanism. Key 94 on flange 96 could provide proper orientation for the outer tube or for the bayonet locking mechanism 86. A suitable cutting window 98 could be provided at the distal end of outer tube 82 in order to produce a workable unit.

The materials chosen may be isotropic or anisotropic. The shear strength of isotropic materials is uniform in all directions while the shear strength of anisotropic materials may be made less in the transverse direction, for example, than in the axial (longitudinal) direction so that the structure could easily transmit torque while still being bendable. Such characteristics may be exhibited by composite materials and the scope of the invention cannot be limited by the specific materials employed or whether or not they possess a particular molecular orientation.

It will be understood by those skilled in the art that numerous modifications and improvements may be made to the preferred embodiment of the invention disclosed herein without departing from the spirit and scope thereof.

TABLE I

Material Properties

| Material | Tensile strength | Modulus elas. (E) | Shear strength (S) |
|---|---|---|---|
| 301 SS hypodermic | 150,000 psi | 28,000,000 psi | 112,500 psi |
| Lexan 121 | 10,000 psi | 350,000 psi (est) | 10,000 psi |
| Ultem 1000 | 15,200 psi | 430,000 psi | 15,000 psi |
| Ultrapek (PAEK) | 24,650 psi | 1,305,000 psi | *18,000 psi |
| PEEK | 13,300 psi | 522,100 psi | 13,800 psi |
| Vectra A130 | 30,000 psi | 2,400,000 psi | 17,800 psi |

*The shear strength value for Ultrapek is an estimate.

TABLE II

Design Properties

| Mat. | Tube Dimensions | Mom. Inert (in.-4th) (I) | Polar Inert (in.-4th) (J) | Sect Modulus (in.-3rd) (Z) | Bend Moment @15 degrees (M) | Def Load (lbf) (W) | Torsion Strength (T) |
|---|---|---|---|---|---|---|---|
| 301 SS | .132 × .106" | 8.706 × 10 − 6 | 1.741 × 10 − 5 | 1.319 × 10 − 4 | 185.3 in-lb | 357.8 | 19.8 in-lb |
| 301 SS | .165 × .145" | 1.468 × 10 − 5 | 2.937 × 10 − 5 | 1.78 × 10 − 4 | 312.6 in-lb | 603.5 | 40.0 in-lb |
| Lexan | .132 × .106" | 8.706 × 10 − 6 | 1.741 × 10 − 5 | 1.319 × 10 − 4 | 2.32 in-lb | 4.5 | 2.64 in-lb |
| Lexan | .132 × .093" | 1.123 × 10 − 5 | 2.246 × 10 − 5 | 1.702 × 10 − 4 | 2.99 in-lb | 5.8 | 3.40 in-lb |
| Lexan | .132 × .076" | 1.327 × 10 − 5 | 2.653 × 10 − 5 | 2.010 × 10 − 4 | 2.53 in-lb | 6.8 | 4.02 in-lb |
| Ultem | .142 × .116" | 1.107 × 10 − 5 | 2.214 × 10 − 5 | 1.559 × 10 − 4 | 3.62 in-lb | 7.0 | 4.68 in-lb |
| Ultem | .139 × .116" | 9.436 × 10 − 6 | 1.887 × 10 − 5 | 1.358 × 10 − 4 | 3.08 in-lb | 6.0 | 4.07 in-lb |
| Ultem | .132 × .106" | 8.706 × 10 − 6 | 1.741 × 10 − 5 | 1.319 × 10 − 4 | 2.85 in-lb | 5.5 | 4.00 in-lb |
| Ultem | .132 × .093" | 1.123 × 10 − 5 | 2.246 × 10 − 5 | 1.702 × 10 − 4 | 3.67 in-lb | 7.1 | 5.10 in-lb |
| Ultem | .132 × .076" | 1.327 × 10 − 5 | 2.653 × 10 − 5 | 2.010 × 10 − 4 | 4.34 in-lb | 8.4 | 6.03 in-lb |
| PAEK | .142 × .116" | 1.107 × 10 − 5 | 2.214 × 10 − 5 | 1.559 × 10 − 4 | 4.88 in-lb | 9.4 | *5.6 in-lb |
| PAEK | .139 × .116" | 9.436 × 10 − 6 | 1.887 × 10 − 5 | 1.358 × 10 − 4 | 4.16 in-lb | 8.0 | *4.9 in-lb |
| PAEK | .132 × .111" | 7.451 × 10 − 6 | 1.490 × 10 − 5 | 1.129 × 10 − 4 | 3.29 in-lb | 6.3 | *4.1 in-lb |
| PAEK | .132 × .106" | 8.706 × 10 − 6 | 1.741 × 10 − 5 | 1.319 × 10 − 4 | 3.84 in-lb | 7.4 | *4.8 in-lb |
| PEEK | 1.42 × .116" | 1.107 × 10 − 5 | 2.214 × 10 − 5 | 1.559 × 10 − 4 | 4.39 in-lb | 8.5 | 4.3 in-lb |
| PEEK | .132 × .093" | 1.123 × 10 − 5 | 2.246 × 10 − 5 | 1.702 × 10 − 4 | 4.46 in-lb | 8.6 | 4.7 in-lb |
| PEEK | .132 × .076" | 1.327 × 10 − 5 | 2.653 × 10 − 5 | 2.010 × 10 − 4 | 5.27 in-lb | 10.2 | 5.5 in-lb |
| Vectra | .132 × .111" | 7.451 × 10 − 6 | 1.490 × 10 − 5 | 1.129 × 10 − 4 | 13.60 in-lb | 26.2 | 4.02 in-lb |
| Vectra | .132 × .106" | 8.706 × 10 − 6 | 1.741 × 10 − 5 | 1.319 × 10 − 4 | 15.88 in-lb | 30.7 | 4.70 in-lb |
| Vectra | .132 × .093" | 1.123 × 10 − 5 | 2.246 × 10 − 5 | 1.702 × 10 − 4 | 20.49 in-lb | 39.6 | 6.06 in-lb |

*The torque value is an estimate for Ultrapek.

What is claimed is:

1. A rotatable elongated inner shaver blade for use with a non-rotatable elongated outer tubular shaver blade comprising:

a non-metallic, torque-transmitting, elongated tubular body having a proximal end and a distal end;

releasable engagement means provided at the proximal end of said tubular body for selectively attaching said tubular body to a means for rotating it about its axis and relative to the outer blade to transmit torque from said means for rotating to the distal end of said tubular body; and a cutting means provided at the distal end of said tubular body for cutting while said tubular body is rotated about its axis, said cutting means having a proximal end and a distal end and comprising at least one projection having a predetermined shape and extending proximally;

attachment means formed at said distal end of said tubular body for attaching said cutting means, said attachment means comprising a projection-receiving recess for engaging said projection and forming therewith a mechanical interlocking connection between said cutting means and said tubular body; and means to prevent the separation of said cutting means from said attachment means.

2. An elongated rotatable shaver blade for attachment to a handpiece having a drive means for rotating a portion of said shaver blade, said shaver blade consisting essentially of:

a non-metallic, non-perforated, elongated tubular inner body having a proximal end and a distal end;

a cutting means for cutting tissue, said cutting means having a cylindrical body similar in diameter to said inner body and immovably secured to the distal end of said inner body;

a rigid, elongated tubular outer body having a proximal end and a distal end and adapted to receive said tubular inner body rotatably therein, said distal end of said outer body provided with a cutting window and adapted-to be placed into, and maintain without reliance on any other structure, a selected predetermined angled orientation relative to said proximal end;

an inner engagement means provided at the proximal end of said tubular inner body for attaching said inner body to said drive, means;

an outer engagement means provided at the proximal end of said tubular outer body for attaching said outer body to said handpiece.

3. An elongated rotatable shaver blade according to claim 2 wherein said cutting means is metallic.

4. An elongated rotatable shaver blade according to claim 2 further comprising:
   at least one proximally extending projection aligned with the cylindrical body of said cutting shell; and
   recess means in the outer surface of said inner member adapted to receive said proximally extending projection; and
   means to form an inseparable connection between said projection and said recess means.

5. A rotatable elongated inner shaver blade for use with a non-rotatable elongated outer tubular shaver blade comprising:
   a non-metallic, torque-transmitting, elongated tubular body having a proximal end and a distal end;
   releasable engagement means unitarily formed together with the proximal end of said non-metallic tubular body for selectively attaching said tubular body to a means for rotating it about its axis and relative to the outer blade to transmit torque from said means for rotating to the distal end of said tubular body; and
   a cutting means provided at the distal end of said tubular body for cutting while said tubular body is rotated about its axis.

6. A rotatable elongated inner shaver blade for use with a non-rotatable elongated outer tubular shaver blade comprising:
   a non-metallic, torque-transmitting, elongated tubular body having a proximal end and a distal end;
   releasable engagement means provided at the proximal end of said non-metallic tubular body for selectively attaching said tubular body to a means for rotating it about its axis and relative to the outer blade to transmit torque from said means for rotating to the distal end of said tubular body; and
   a cutting means unitarily formed together with the distal end of said tubular body for cutting while said tubular body is rotated about its axis.

7. A rotatable elongated inner shaver blade according to claim 6 wherein said engagement means is unitarily formed together with said non-metallic tubular body.

8. In combination, a rotatable elongated inner shaver blade and an angled, non-roatable outer tubular shaver blade, the inner shaver blade comprising:
   a non-metallic, elongated tubular body having a proximal end and a distal end and adapted to be rotatably received within the outer shaver blade, said tubular body having a first predetermined rigidity which makes it sufficiently flexible to rotate within said outer shaver blade;
   an engagement means provided at the proximal end of said tubular body for attaching said body to a means for rotation; and
   a cutting means provided at the distal end of said tubular body;
   said angled non-rotatable outer tubular shaver blade comprising:
   a non-metallic elongated tubular hollow sheath having a proximal end and a distal end, said sheath having a second predetermined rigidity greater than said first predetermined rigidity and adapted to be placed into, and maintain without reliance on any other structure, a selected predetermined angled orientation relative to said proximal end;
   an engagement means attached to the proximal end of said hollow sheath for attaching said hollow sheath to a means for holding it rotationally fixed relative to said tubular body; and
   a window means provided at the distal end of said sheath for providing access for said cutting means to the exterior of said sheath.

9. A rotatable elongated inner shaver blade for use with a non-rotatable elongated outer tubular shaver blade comprising:
   a non-metallic, torque-transmitting, elongated tubular body having a proximal end and a distal end, said tubular body made from a material selected from the group consisting of polycarbonate, polyetherimide, polyalphaetherketone and polyetheretherketone;
   releasable engagement means unitarily formed together with the proximal end of said non-metallic tubular body for selectively attaching said tubular body to a means for rotating it about its axis and relative to the outer blade to transmit torque from said means for rotating to the distal end of said tubular body; and
   a cutting means provided at the distal end of said tubular body for cutting while said tubular body is rotated about its axis.

10. An elongated rotatable shaver blade according to claim 2 wherein said distal end of said elongated tubular outer body is obliquely oriented relative to the proximal end of said elongated tubular outer body and wherein said elongated tubular inner body and said cutting means are selectively removable as a unit from within said elongated tubular outer body.

\* \* \* \* \*